United States Patent

Weissenfluh et al.

Patent Number: 5,584,692
Date of Patent: Dec. 17, 1996

[54] TENSIONING GRIPPER FOR ONDOTOLOGICAL USE

[75] Inventors: Hans v. Weissenfluh, Magadino; Beat A. v. Weissenfluh, Gentilino, both of Switzerland

[73] Assignee: Hawe Neos Dental Dr. H. v. Weissenfluh AG, Bioggio, Switzerland

[21] Appl. No.: 493,155

[22] Filed: Jun. 21, 1995

[30] Foreign Application Priority Data

Jun. 21, 1994 [CH] Switzerland ............... 01955/94

[51] Int. Cl.$^6$ ................................................. A61C 5/04
[52] U.S. Cl. ...................................... 433/155; 433/39
[58] Field of Search ................................ 433/155, 39

[56] References Cited

U.S. PATENT DOCUMENTS

| | | | |
|---|---|---|---|
| 1,359,665 | 11/1920 | Borkin | 433/155 |
| 2,218,774 | 10/1940 | Strell . | |
| 2,595,850 | 5/1952 | Hicks . | |
| 2,687,573 | 8/1954 | Stone | 433/155 |
| 2,995,822 | 8/1961 | Tofflemire | 433/155 |
| 4,396,374 | 8/1983 | Ericson | 433/39 |
| 4,551,097 | 11/1985 | Lazarus | 433/39 |

FOREIGN PATENT DOCUMENTS

9409716  5/1994  WIPO ............... 433/155

*Primary Examiner*—Nicholas D. Lucchesi
*Attorney, Agent, or Firm*—Marks & Murase L.L.P.

[57] ABSTRACT

In a tensioning gripper with a ring and a coaxially arranged rotary pin, both the ring and the pin are provided with a slot suitable for receiving a matrix to be tensioned. The slot of the rotary pin has a symmetry plane parallel to the longitudinal axis of the rotary pin. The sides of the slot are composed by two angled portions which are arranged symmetrically on both sides of the symmetry plane and both portions converge towards the longitudinal axis of the rotary pin, the two vertices of the portions being opposite and adjacent one another. Such a slot allows easy introduction and gripping of the matrix until, by rotating the pin, the matrix is held and tensioned.

10 Claims, 2 Drawing Sheets

5,584,692

TENSIONING GRIPPER FOR ONDOTOLOGICAL USE

BACKGROUND OF THE INVENTION

The present invention relates to a tensioning gripper for gripping and tensioning a matrix used for dental reconstruction in odontology, in particular of the type suitable for being actuated by means of a tensioning device similar, e.g., to the device disclosed by the same Applicant in prior patent application PCT/EP93/02940.

Such a type of tensioning gripper consists of an external ring of relatively rigid material coupled to a coaxial rotary pin. Both the ring and the pin are provided with one or more slots which are suitable to receive the matrix to be tensioned, which is driven by the rotary pin, winding it and remaining fastened to it.

Due to the small size of the tensioning gripper on which the operator must work, sometimes introducing the matrix into the slot of the rotary pin can be difficult, and it is still more difficult to keep said matrix fastened to its interior in a reliable enough way in order that it may be driven by the rotary pin without slipping out or getting disengaged, thus obliging the operator to repeat the whole procedure.

SUMMARY OF THE INVENTION

It is the object of the present invention to present a tensioning gripper with which it is easy for the operator to introduce the matrix to be tensioned and which secures the matrix until it is wound up for tensioning. This object is attained with a tensioning gripper for a matrix tensioning apparatus for odontological use, comprising a ring and a rotary pin coaxially arranged inside said ring, with both said pin and said ring being provided with at least one slot suitable for receiving the ends of the matrix to be tensioned, wherein the slot through the rotary pin has a symmetry plane parallel to the longitudinal axis of said rotary pin, whereas each side of the slot is composed of two angled portions, said sides being arranged mirror-like on both sides of said symmetry plane and both portions converging towards said longitudinal axis of said rotary pin, the vertices of the portions being opposite and adjacent one to the other.

BRIEF DESCRIPTION OF THE DRAWINGS

The functional features of the tensioning gripper according to the present invention and the advantages which can be obtained by means of it are disclosed hereinafter in greater detail by referring to the accompanying drawings.

The above figures only represent a preferred embodiment which shall not be construed as being binding or limiting relatively to other embodiments in which the several components have different shapes or sizes.

DETAILED DESCRIPTION OF THE INVENTION

Figure 1:
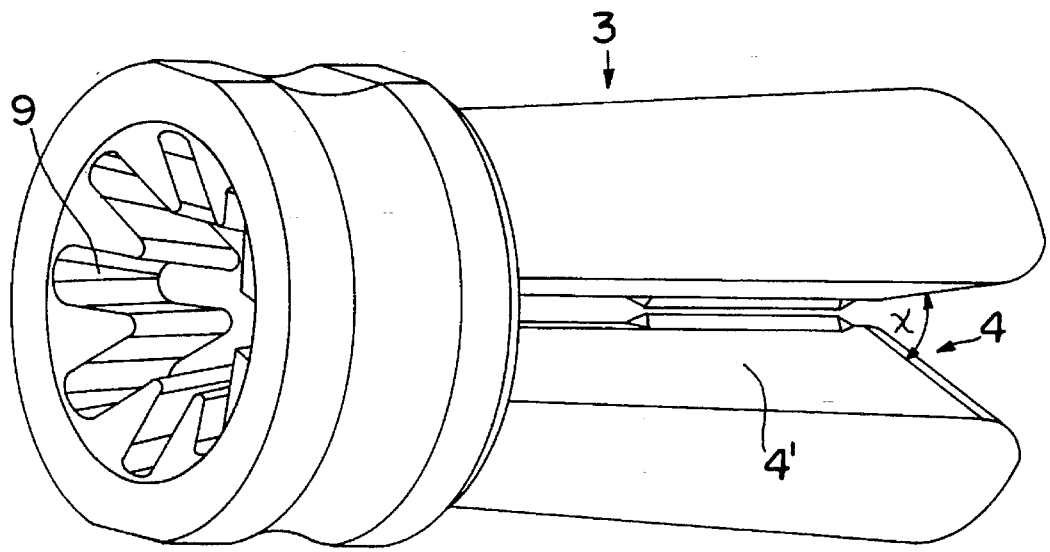
FIG. 1 shows a perspective view of the rotary pin of a preferred embodiment of the tensioning gripper according to the present invention.

FIG. 1 shows a rotary pin 3 of an exemplary tensioning gripper according to the present invention which is similar to the rotary pins known from the prior art as regards both its outer shape and the small crown gear 9 suitable for coupling with an appropriate tensioning apparatus.

Figures 3, 4:
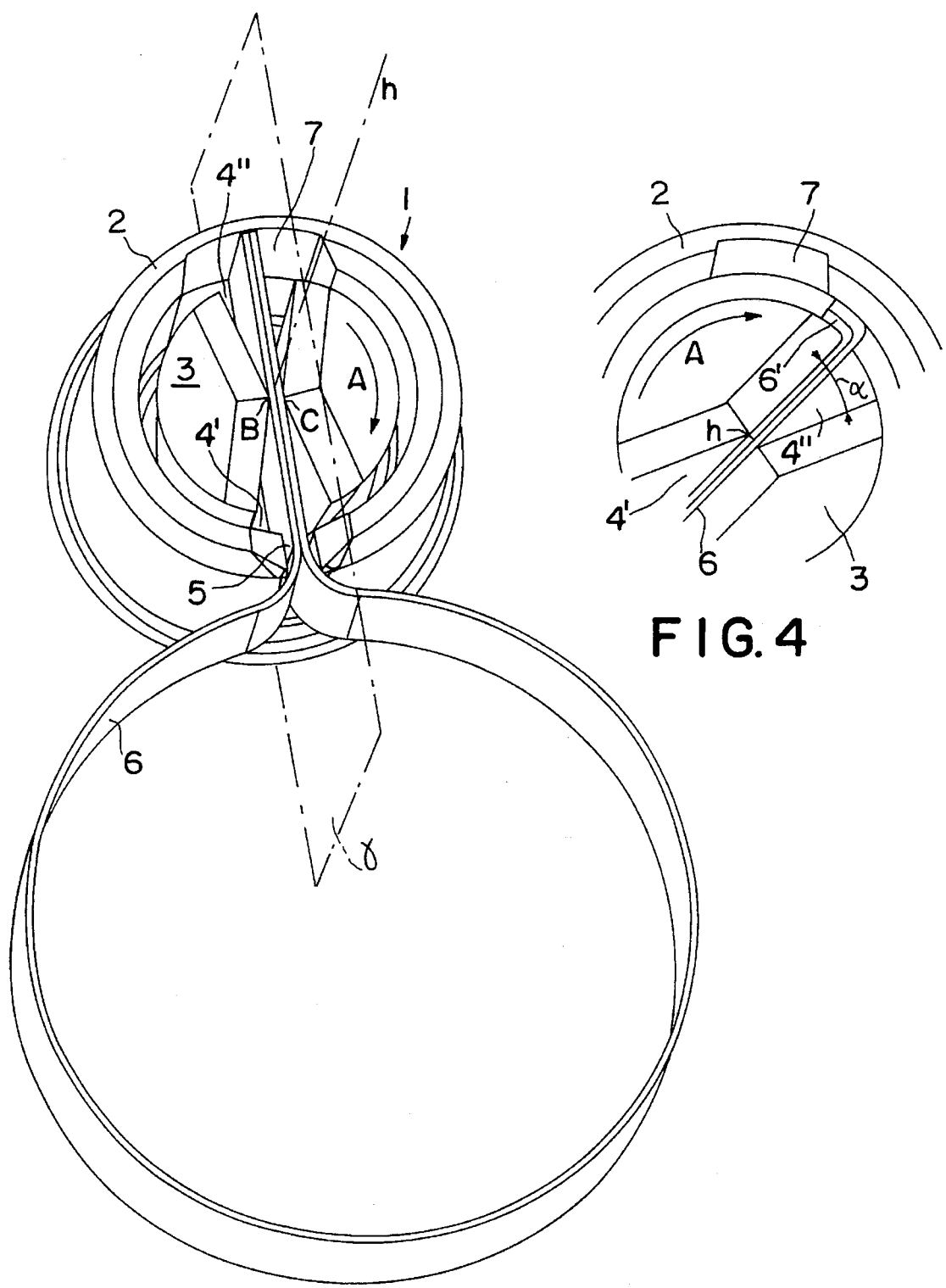
FIG. 3 shows a perspective view of the whole tensioning gripper according to the present invention, with a matrix entered in it.
FIG. 4 shows a partial plan view of the tensioning gripper with the ends of the matrix following the rotation of the rotary pin.

The through going slot 4 of the pin 3, on the contrary, is different, and, as one will observe on considering FIG. 1 together with FIG. 3, the slot 4 is symmetrical relative to a plane γ passing through, is arranged parallel to the longitudinal axis "h" of the pin 3 and is composed of two sides having each two angled portions 4' 4" arranged substantially mirror-like. The portions 4', 4" converge towards longitudinal axis h of the pin, with each pair of adjacent portions generating a vertex B, or C. The gap between the two vertices B and C is smaller than the double thickness of the matrix and is able to clamp the ends of the matrix, because its sides are slightly resilient.

According to the preferred embodiment as displayed in the accompanying figures, the angle α formed by two mutually opposite convergent portions of the sides is approximately 30°, see FIG. 4.

By suitably dimensioning slot 4 the introduction of the matrix 6 is made easier because the slot sides diverge outwards. The result is obtained that the matrix 6, after having been pushed beyond the longitudinal axis h of pin 3, remains gripped in this position by the effect of the pressure applied by the sides at the vertices B and C. All the above allows the process of winding and tensioning matrix 6 to be started more reliably and rapidly.

In order to further increase the retaining engagement of the matrix 6 on the rotary pin 3, the inner surface of the ring 2 of the tensioning gripper 1 can be provided with a groove 7, facing the rotary pin 3 (FIGS. 3 and 4). By providing such a groove 7 in a diametrically opposite position across from the position of slot 5, which is one of the plurality of slots provided through the ring 2 for the matrix to enter (in the embodiment displayed herein, only one slot is present). If the matrix 6 is introduced until it comes to rest against the concave portion of groove 7, even after a limited initial rotation of the rotary pin 3 for example in the direction of arrows A, the end portions of the matrix 6 which initially protruded into groove 7 are so bent during the rotation (FIG. 4), as to come to lay inside the gap existing between the inner wall of the ring 2 and the outer surface of the pin 3, thus forming an edge 6' which prevents the matrix 6 from slipping in the opposite direction out of the tensioning gripper 1. By operating in that way the matrix 6 can be provided with an effective mechanical retaining means, more reliable than is offered by simple friction, or equivalent means.

By providing a tensioning gripper 1 in which both the groove 7 on the ring 2 and the particularly shaped slot 4 of the rotary pin 3 are provided, an advantageous result is obtained as regards the rapidity and reliability of the whole matrix tensioning procedure.

Figure 2:
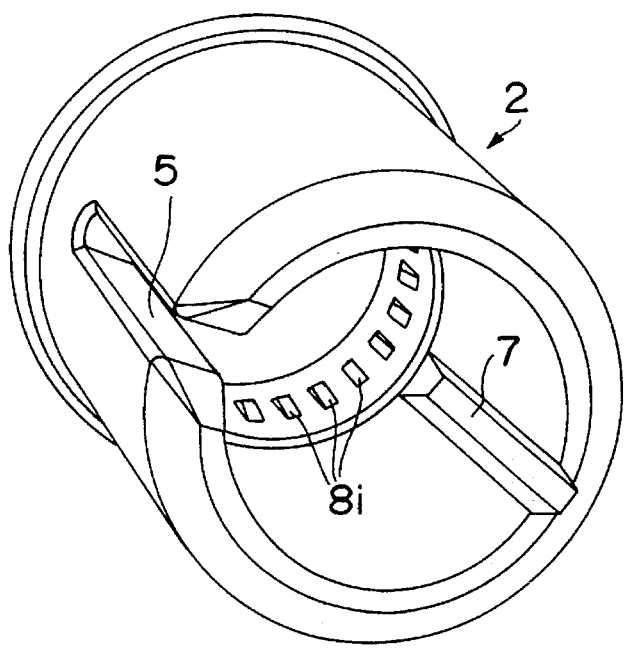
FIG. 2 shows a perspective view of the ring of the same embodiment of FIG. 1.

In a further improvement there is an elastic, limitedly forced coupling between the ring 2 and the rotary pin 3. Instead of producing such a coupling by means of expensive precise dimensions during the moulding step of above said components, which is difficult to control precisely, the inner surface of ring 2 is provided with a plurality of peripherally arranged protrusions 8i (FIG. 2). These protusions are plastically deformable to a prefixed extent when, between them, the rotary pin 3 having an outer diameter which is slightly greater than the diameter of the externally tangent circumference of said protrusions 8*i* is introduced. As a consequence of that, said protusions 8*i* are slightly deformed by compression and act as support means for the rotary pin 3.

As already briefly mentioned, it is evident that one skilled of the art can envisage other embodiments which are different from those disclosed and represented up to here.

We claim:

1. Tensioning gripper for applying tension to a matrix for odontological use, comprising:

a ring; and a rotary pin coaxially arranged inside said ring;

wherein said pin and said ring are each provided with at least one slot suitable for receiving the ends of a matrix to be tensioned;

wherein the at least one slot of the rotary pin has a symmetry plane parallel to the longitudinal axis of said rotary pin and each side of said at least one slot through the rotary pin is composed of two angled portions, said sides being arranged symmetrically on both sides of said symmetry plane, and both sides of said at least one slot of said pin converging towards said longitudinal axis of said rotary pin, the vertices of the angled portions being opposite and adjacent to one another.

2. Tensioning gripper according to claim 1, in which converging sides of said at least one slot in the rotary pin form, between them, an angle of approximately 30°.

3. Tensioning gripper according to claim 1, wherein said ring is provided, on its inner surface facing said rotary pin and in a diametrically opposite position to the position of said at least one slot in the ring, with a groove at least extending throughout the height of that portion of the ring which is frontally opposite to one of said portions which constitute said slot in the rotary pin.

4. Tensioning gripper according to claim 1, wherein the inner surface of the ring is peripherally provided with a plurality of protrusions which are plastically deformable to a prefixed extent when said rotary pin is introduced between them.

5. Tensioning gripper according to claim 1, wherein the distance between said vertices is less than twice the thickness of said matrix.

6. A method of applying tension to a matrix for odontological use, comprising the steps of;

inserting a rotary pin coaxially inside a ring;

providing said pin and said ring with at least one slot for receiving a matrix;

inserting said matrix is said at least one slot; and turning said pin to apply tension to said matrix;

wherein the at least one slot through the rotary pin has a symmetry plane parallel to the longitudinal axis of said rotary pin and each side of said at least one slot through the rotary pin is composed of two angled portions, said sides being arranged symmetrically on both sides of said symmetry plane, and both sides of said at least one slot of said pin converging towards said longitudinal axis of said rotary pin, the vertices of the angled portions being opposite and adjacent one to the other.

7. A method according to claim 6, wherein the converging sides at least one of said slot through the rotary pin form, between them, an angle of approximately 30°.

8. A method according to claim 6, further comprising the steps of;

providing a groove on an inner surface of said ring which is opposite the position of the at least one slot provided in said ring;

inserting said matrix in said groove after it has been inserted through said at least one slot in said ring and pin, prior to turning said pin; and turning said pin to bend an end of said matrix inserted in said groove to secure said matrix.

9. A method according to claim 6, further comprising the step of providing a plurality of protrusions which are plastically deformable to a predetermined extent on the inner surface of said ring.

10. A method according to claim 6, wherein the distance between said vertices is less than twice the thickness of said matrix.

* * * * *